(12) United States Patent
Yamada et al.

(10) Patent No.: US 11,497,693 B2
(45) Date of Patent: Nov. 15, 2022

(54) COSMETIC COMPOSITION FOR KERATIN FIBERS AND MANUFACTURING METHOD THEREOF

(71) Applicant: L'OREAL, Paris (FR)

(72) Inventors: Hidetoshi Yamada, Fucyu (JP); Daisuke Misu, Yokohama (JP); Satoshi Kitano, Tokyo (JP)

(73) Assignee: L'OREAL, Paris (FR)

( * ) Notice: Subject to any disclaimer, the term of this patent is extended or adjusted under 35 U.S.C. 154(b) by 8 days.

(21) Appl. No.: 15/533,156

(22) PCT Filed: Dec. 8, 2015

(86) PCT No.: PCT/JP2015/084867
§ 371 (c)(1),
(2) Date: Jun. 5, 2017

(87) PCT Pub. No.: WO2016/093363
PCT Pub. Date: Jun. 16, 2016

(65) Prior Publication Data
US 2017/0333306 A1 Nov. 23, 2017

(30) Foreign Application Priority Data
Dec. 8, 2014 (JP) .............................. JP2014-247789

(51) Int. Cl.
| | |
|---|---|
| *A61K 8/34* | (2006.01) |
| *A61K 8/36* | (2006.01) |
| *A61K 8/06* | (2006.01) |
| *A61K 8/19* | (2006.01) |
| *A61K 8/44* | (2006.01) |
| *A61Q 5/04* | (2006.01) |
| *A61Q 5/10* | (2006.01) |
| *A61K 8/39* | (2006.01) |
| *A61K 8/86* | (2006.01) |
| *A61K 8/42* | (2006.01) |
| *A61K 8/55* | (2006.01) |

(52) U.S. Cl.
CPC .................. *A61K 8/19* (2013.01); *A61K 8/06* (2013.01); *A61K 8/342* (2013.01); *A61K 8/36* (2013.01); *A61K 8/361* (2013.01); *A61K 8/39* (2013.01); *A61K 8/42* (2013.01); *A61K 8/44* (2013.01); *A61K 8/55* (2013.01); *A61K 8/86* (2013.01); *A61Q 5/04* (2013.01); *A61Q 5/10* (2013.01); *A61K 2800/882* (2013.01)

(58) Field of Classification Search
None
See application file for complete search history.

(56) References Cited

U.S. PATENT DOCUMENTS

| | | | |
|---|---|---|---|
| 4,314,807 A * | 2/1982 | Grollier | A61K 8/046 8/406 |
| 4,981,845 A * | 1/1991 | Pereira | A61K 8/06 514/558 |
| 6,277,154 B1 | 8/2001 | Lorenz | |
| 6,903,057 B1 * | 6/2005 | Tsaur | A61K 8/732 510/130 |
| 7,071,151 B2 * | 7/2006 | Dykstra | A61K 8/37 510/107 |
| 7,374,582 B2 * | 5/2008 | Allard | A61K 8/362 8/405 |
| 2004/0234471 A1 | 11/2004 | Corbella et al. | |
| 2009/0004122 A1 * | 1/2009 | Modak | A61K 8/345 424/49 |
| 2014/0026332 A1 | 1/2014 | Jo et al. | |

FOREIGN PATENT DOCUMENTS

| | | |
|---|---|---|
| DE | 102004025281 A1 | 12/2005 |
| EP | 0134483 * | 3/1985 |
| GB | 2451885 A | 2/2009 |
| JP | 2004-269503 A | 9/2004 |
| JP | 2008-156252 A | 7/2008 |
| JP | 2010-254633 A | 11/2010 |
| JP | 2013-503109 A | 1/2013 |
| WO | 2011/024300 A1 | 3/2011 |
| WO | 2011/034868 A1 | 3/2011 |
| WO | 2013/160257 A2 | 10/2013 |

OTHER PUBLICATIONS

Mitsui, Takeo, New Cosmetic Science Second Edition, p. 368.
International Search Report for PCT/JP2015/084867, dated Feb. 23, 2016.
Tsubonishi, Makoto et al., "Alkali-containing first solutions for two-component oxidative hair dyes or bleaches," Chemical Abstracts Service, XP002754031, Database accession No. 153:588731.
Machine Translation of Notice of Opposition for EP Patent No. 3,244,874, filed Jun. 23, 2021.

* cited by examiner

*Primary Examiner* — Jennifer A Berrios
(74) *Attorney, Agent, or Firm* — Marbury Law Group, PLLC.

(57) ABSTRACT

The present invention relates to a composition for keratin fibers comprising: (a) at least one non-neutralized anionic surfactant; (b) at least one non-ionic surfactant; (c) at least one fatty alcohol; and (d) at least one alkaline agent, wherein the composition does not comprise more than 2% by weight of a phosphoric surfactant. The present invention can provide the composition for keratin fibers which can suppress its ammonium odor and have improved stability.

17 Claims, 1 Drawing Sheet

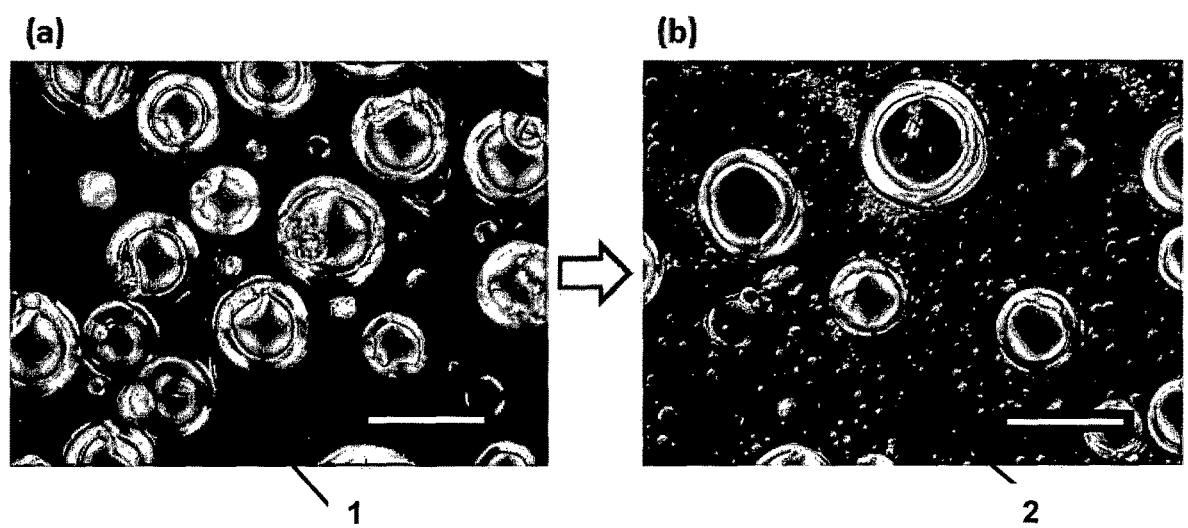

COSMETIC COMPOSITION FOR KERATIN FIBERS AND MANUFACTURING METHOD THEREOF

CROSS REFERENCE TO RELATED APPLICATIONS

This is a national stage application of PCT/JP2015/084867, filed internationally on Dec. 8, 2015, which claims priority to Japanese Application No. 2014-247789, filed on Dec. 8, 2014, both of which are incorporated by reference herein in their entireties.

TECHNICAL FIELD

The present invention relates to a cosmetic composition for keratin fibers. The present invention also relates to a method for manufacturing the cosmetic composition.

BACKGROUND ART

A cosmetic composition for keratin fibers, such as hair, for example, a hair coloring agent and a hair permanent waving agent, includes an alkaline agent. As the alkaline agent, ammonia is commonly used due to its safety and performance during cosmetic treatments for keratin fibers.

However, ammonia has an offensive odor, and this offensive odor has been a big drawback in the use of ammonia. Therefore, the elimination of ammonia odor from cosmetic compositions for keratin fibers containing ammonia is one of the important targets nowadays in the field.

To date, some prior art documents relating to cosmetic compositions for keratin fibers, which include ammonia as the alkaline agent, have been published.

WO 2011/024300 discloses a cosmetic composition for keratin fibers, comprising (a) at least one phosphoric surfactant; (b) at least one non-ionic surfactant; (c) at least one polyol; (d) at least one oil; and (e) at least one alkaline agent. JPT-2013-503109 also discloses a cosmetic composition which is useful because it does not generate odor and maintains a level of cosmetic performance comparative to that of conventional cosmetic compositions.

JPA-2008-156252 discloses a oxidation hair dye comprising an oxidation dye composition and an oxidizing agent composition, wherein the oxidation dye composition contains, in addition to an oxidation dye, an alkaline agent and water, (A) a phosphoric ester-based compound, (B) a non-ionic surfactant, (C) a higher fatty acid, (D) a $C_{12}$ to $C_{18}$ higher alcohol and (E) at least one kind of oil-based ingredient selected from a fatty acid ester, an α-olefin oligomer and liquid paraffin, to provide an oxidation hair dye readily usable without waste.

WO 2011/034868 discloses a hair colouring or bleaching composition comprising an oxidizing agent, and a gel network thickening system comprising i) a first surfactant component selected from $C_{14}$ to $C_{30}$ alkyl phosphate, $C_{14}$ to $C_{30}$ alkyl ether phosphate or mixtures thereof, ii) a second component selected from $C_{14}$ to $C_{30}$ fatty alcohols, and iii) a third surfactant component selected from polyoxyethylene $C_8$ to $C_{30}$ alkyl ethers, to provide hair colourant and bleaching compositions which deliver lightening and colour, are easy to manufacture, and improve adhesion of the composition to the hair roots.

However, there is still a need for a cosmetic composition for keratin fibers that includes an alkaline agent which can suppress ammonium odor.

DISCLOSURE OF INVENTION

An objective of the present invention is to provide the composition for keratin fibers, such as hair, with reduced odor of ammonia.

Another objective of the present invention is to establish a method for manufacturing a composition for keratin fibers with reduced odor of ammonia.

The above objective of the present invention can be achieved by a composition for keratin fibers, such as hair, comprising:
(a) at least one non-neutralized anionic surfactant;
(b) at least one non-ionic surfactant;
(c) at least one fatty alcohol; and
(d) at least one alkaline agent,
wherein the composition does not comprise more than 2% by weight, preferably 1% by weight, more preferably 0.2% by weight of a phosphoric surfactant.

Preferably, the composition is in a form of an emulsion.

Preferably, the (d) alkaline agent comprises ammonia and/or salts thereof.

Preferably, the (a) non-neutralized anionic surfactant is a carboxylic acid type surfactant.

In particular, the (a) non-neutralized anionic surfactant may be chosen from a group consisting of fatty carboxylic acid, fatty ether carboxylic acid, N-acylamino acids, anionic derivatives of proteins, and mixtures thereof.

It is preferable that the (b) non-ionic surfactant is chosen from monooxyalkylenated, polyoxyalkylenated, monoglycerolated or polyglycerolated nonionic surfactants or the mixtures thereof.

It is preferable that the (c) fatty alcohol has a structure R—OH wherein R is chosen from saturated and unsaturated, linear and branched radicals containing from 8 to 40 carbon atoms.

It is preferable that the composition has 3 Pas or more of viscosity at 25° C.

The present invention also relates to a composition for keratin fibers prepared by mixing:
(a) at least one non-neutralized anionic surfactant;
(b) at least one non-ionic surfactant;
(c) at least one fatty alcohol; and
(d) at least one alkaline agent.

Preferably, components (a) to (c) are mixed first, and then component (d) is mixed.

The present invention also relates to a method for preparing a composition for keratin fibers comprising steps of:
(i) mixing (a) at least one non-neutralized anionic surfactant, (b) at least one non-ionic surfactant and (c) at least one fatty alcohol to prepare an oil phase,
(ii) mixing the oil phase obtained in step (i) with aqueous phase to prepare an emulsion, and
(iii) adding (d) at least one alkaline agent to the emulsion obtained in step (ii).

Preferably, the steps (i) and (ii) are carried out at a temperature from 40 to 95° C., preferably from 50 to 90° C., and the step (iii) is carried out at a temperature of more than 0 to 40° C., preferably from 10 to 30° C.

Preferably, the pH value of the emulsion in the step (ii) is below 9.0, preferably below 8.0, more preferably below 7.0.

BRIEF DESCRIPTION OF DRAWINGS

FIG. 1 shows a microscopic photography of the mixture of the composition prepared in the example. FIG. 1(a) shows the emulsion before the alkaline agents were added. FIG.

1(b) shows the composition after the alkaline agents were added and mixed. In both figures, scale bar is 50 μm.

BEST MODE FOR CARRYING OUT THE INVENTION

The inventor performed diligent research and surprisingly found that the composition for keratin fibers according to present invention can suppress its ammonium odor.

(I) The Composition

Thus, the composition according to the present invention is for keratin fibers, such as hair, and comprises:
(a) at least one non-neutralized anionic surfactant;
(b) at least one non-ionic surfactant;
(c) at least one fatty alcohol; and
(d) at least one alkaline agent.

Furthermore, the composition according to present invention does not comprise more than 2% by weight, preferably 1% by weight, more preferably 0.2% by weight of a phosphoric surfactant.

According to the composition for keratin fibers of the present invention, it can reduce ammonia odor generated from the composition.

Hereinafter, the composition according to the present invention will be explained in a more detailed manner.

(a) Non-Neutralized Anionic Surfactant

The term "non-neutralized anionic surfactant" means an anionic surfactant which is not neutralized. In other words, the term "non-neutralized anionic surfactant" means an anionic surfactant in which a proton of its hydrophilic functional group is not dissociated. Therefore, the non-neutralized anionic surfactant is in an acid form, and is not a salt form or in an ionized form. Two or more non-neutralized anionic surfactant may be used. Thus, a single type of non-neutralized anionic surfactant or a combination of different types of non-neutralized anionic surfactants may be used.

The non-neutralized anionic surfactants which may be used in the present invention may include carboxylic acid type surfactants, sulfonic acid type surfactants, and sulfuric acid ester type surfactants. Preferably, the non-neutralized anionic surfactants are carboxylic acid type surfactants.

The carboxylic acid type surfactants which can be used in the present invention may include, but not limited to, fatty carboxylic acids, fatty ether carboxylic acids, N-acylamino acids, and anionic derivatives of proteins.

Non-limiting examples of the fatty carboxylic acids includes fatty acids having from 6 to 40, preferably from 8 to 36, more preferably from 10 to 32, even more preferably from 12 to 28 carbon atoms corresponding formula (I)

$$RCOOH \qquad (I)$$

wherein:
R is a hydrocarbon radical containing from 6 to 40 carbon atoms. In addition, R may be linear or branched, acyclic or cyclic, saturated or unsaturated, aliphatic or aromatic, substituted or unsubstituted. Typically, R is a linear or branched, acyclic $C_6$-$C_{40}$ alkyl or alkenyl group or a $C_1$-$C_{40}$ alkyl phenyl group, more typically a $C_8$-$C_{24}$ alkyl or alkenyl group or a $C_4$-$C_{20}$ alkyl phenyl group, and even more typically a $C_{10}$-$C_{18}$ alkyl group or alkenyl group or a $C_6$-$C_{16}$ alkyl phenyl group, which may be substituted. As examples of the substituent, mention may be made of a monovalent functional group such as a halogen atom, a hydroxyl group, a $C_1$-$C_6$ alkoxy group, an amino group, a $C_1$-$C_6$ alkylamino group, a $C_1$-$C_6$ dialkylamino group, a nitro group, a carbonyl group, an acyl group, a carboxyl group, a cyano group and the like.

Suitable fatty carboxylic acids having from 6 to 40 carbon atoms include, but are not limited to, the following representatives referred to by their INCI names (INCI: nomenclature for raw materials according to the International Cosmetic Ingredient Dictionary, 10th Edition, published by the Cosmetic, Toiletry and Fragrance Association Inc. (CTFA), Washington D.C., USA): arachidic acid, arachidonic acid, beeswax acid, capric acid, caproic acid, caprylic acid, coconut acid, isostearic acid, lauric acid, linoleic acid, linolenic acid, myristic acid, oleic acid, olive acid, palmitic acid, rapeseed acid, stearic acid, tallow acid, undecanoic acid, undecylenic acid or wheat germ acid and mixtures thereof. Preferably, the fatty carboxylic acids having from 6 to 40 carbon atoms are capric acid, caprylic acid, lauric acid, oleic acid, isostearic acid, or stearic acid.

The fatty ether carboxylic acids can indicate compounds in which a carboxylic acid group bounds to a hydrophobic group via polyoxyalkylene units or glycol ether units, and may include, but not limited to, polyoxyalkylenated alkyl ether carboxylic acids, polyoxyalkylenated alkylaryl ether carboxylic acids, polyoxyalkylenated alkylamido ether carboxylic acids, and alkyl glycol carboxylic acids.

Non-limiting examples of the fatty ether carboxylic acids include compounds corresponding to formula (II):

$$RO[CH_2O]_u[(CH_2)_xCH(R')(CH_2)_y(CH_2)_zO]_v[CH_2CH_2O]_wCH_2COOH \qquad (II)$$

wherein:
R is a hydrocarbon radical containing from 6 to 40 carbon atoms;
u, v and w, independently of one another, represent numbers of from 0 to 60;
x, y and z, independently of one another, represent numbers of from 0 to 13;
R' represents hydrogen, alkyl, preferably $C_1$-$C_{12}$ alkyl; and the sum of x+y+z is 0 or more.

The fatty ether carboxylic acids corresponding to formula (II) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (II), R is linear or branched, acyclic or cyclic, saturated or unsaturated, aliphatic or aromatic, substituted or unsubstituted. As examples of the substituent, mention may be made of a monovalent functional group such as a halogen atom, a hydroxyl group, a $C_1$-$C_6$ alkoxy group, an amino group, a $C_1$-$C_6$ alkylamino group, a $C_1$-$C_6$ dialkylamino group, a nitro group, a carbonyl group, an acyl group, a carboxyl group, a cyano group and the like. Typically, R is a linear or branched, acyclic $C_6$-$C_{40}$ alkyl or alkenyl group or a $C_1$-$C_{40}$ alkyl phenyl group, more typically a $C_8$-$C_{24}$ alkyl or alkenyl group or a $C_4$-$C_{20}$ alkyl phenyl group, and even more typically a $C_{10}$-$C_{18}$ alkyl group or alkenyl group or a $C_6$-$C_{16}$ alkyl phenyl group, which may be substituted; u, v, w, independently of one another, is typically a number from 2 to 20, more typically a number from 3 to 17, and most typically a number from 5 to 15; x, y, z, independently of one another, is typically a number from 2 to 13, more typically a number from 1 to 10, and most typically a number from 0 to 8;

Suitable fatty ether carboxylic acids include, but are not limited to, the following representatives referred to by their INCI names: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, $C_{11}$-$C_{15}$ Pareth-7 Carboxylic Acid, C12-13 Pareth-5 Carboxylic Acid, $C_{12}$-$C_{13}$ Pareth-8 Carboxylic Acid, $C_{12}$-$C_{13}$ Pareth-12 Carboxylic Acid, $C_{12}$-$C_{15}$ Pareth-7 Carboxylic Acid, $C_{12}$-$C_{15}$ Pareth-8 Carboxylic Acid, $C_{14}$-$C_{15}$ Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid, and mixtures thereof.

Preferably, the fatty ether carboxylic acids are Oleth-10 Carboxylic Acid, Laureth-5 Carboxylic Acid, and Laureth-11 Carboxylic Acid.

Typically the polyoxyalkylenated alkyl ether carboxylic acids, polyoxyalkylenated alkylaryl ether carboxylic acids, and polyoxyalkylenated alkylamido ether carboxylic acids include 2 to 50, preferably 2 to 10, more preferably 2 to 5 of ethylene oxide units. The alkyl group included in these compounds is typically $C_4$-$C_{30}$, preferably $C_6$-$C_{28}$, more preferably $C_8$-$C_{24}$ alkyl group.

Non-limiting examples of the polyoxyalkylenated alkyl ether carboxylic acids are oxyethylenated (6EO) lauryl ether carboxylic acid and oxyethylenated (6EO) tridecyl ether carboxylic acid. Non-limiting example of the amido ether carboxylic acids is lauryl amido ether carboxylic acid (3EO).

The alkyl group included in the alkyl glycol carboxylic acids is typically $C_4$-$C_{30}$, preferably $C_6$-$C_{28}$, more preferably $C_8$-$C_{24}$ alkyl group. Non-limiting example of the alkyl glycol carboxylic acids is lauryl glycol carboxylic acid.

The amino acids which may compose the N-acylamino acids can be amino acids including a carboxylic acid. The amino acids can be typically chosen from the group consisting of glutamic acid, aspartic acid, alanine, lysine, sarcosine, and their mixtures.

The acyl group which may compose the N-acylamino acids can be represented by R'C=O, wherein R' represents a saturated or unsaturated, linear or branched, hydrocarbon chain, preferably comprising from 10 to 30 carbon atoms, preferably from 12 to 22 carbon atoms, preferably from 14 to 22 carbon atoms and better still from 16 to 20 carbon atoms. The acyl group can be typically chosen from the group consisting of lauroyl, myristoyl, behenoyl, palmitoyl, stearoyl, isostearoyl, olivoyl, cocoyl or oleoyl groups, and their mixtures.

Non-limiting examples of the N-acylamino acids include cocoyl glutamic acid, lauroyl glutamic acid, myristoyl glutamic acid, stearoyl glutamic acid, lauroyl aspartic acid, cocoyl alanine, lauroyl alanine, cocoyl sarcosine, myristoyl sarcosine, lauroyl sarcosine, palmitoyl sarcosine, and lauroyl lysine.

N-acylamino acids include their derivatives, such as N-acylalkyl ($C_1$-$C_{12}$) amino acids. Non-limiting examples of the N-acylalkyl ($C_1$-$C_{12}$) amino acids include lauroyl methyl-β-alanine and myristoyl methyl-β-alanine.

Preferably, the N-acylamino acids are cocoyl glutamic acid, cocoyl sarcosine, lauroyl methyl-βalanine, and myristoyl methyl-β-alanine.

The anionic derivatives of proteins are protein hydrolysates comprising a hydrophobic group, it being possible for the said hydrophobic group to be naturally present in the protein or to be added by reaction of the protein and/or of the protein hydrolysate with a hydrophobic compound. The proteins are of vegetable origin or derived from silk, and the hydrophobic group can in particular be a fatty chain, for example an alkyl chain comprising from 10 to 22 carbon atoms. Mention may more particularly be made, as anionic derivatives of proteins of vegetable origin, of apple, wheat, soybean or oat protein hydrolysates comprising an alkyl chain having from 10 to 22 carbon atoms, and their salts. The alkyl chain can in particular be a lauryl chain and the salt can be a sodium, potassium and/or ammonium salt.

Thus, mention may be made, as protein hydrolysates comprising a hydrophobic group, for example, of protein hydrolysates where the protein is a silk protein modified by lauric acid; protein hydrolysates where the protein is a wheat protein modified by lauric acid; protein hydrolysates where the protein is an oat protein comprising an alkyl chain having from 10 to 22 carbon atoms and more especially protein hydrolysates where the protein is an oat protein modified by lauric acid; or apple protein hydrolysates comprising an alkyl chain having from 10 to 22 carbon atoms.

Other carboxylic acid type surfactants includes, for example, ($C_8$-$C_{20}$) acyl lactic acids and ($C_6$-$C_{30}$) alkyl-D-galactosiduronic acids.

The sulfonic acid type surfactants, which may be used in the present invention, may include, but not limited to, ($C_6$-$C_{30}$)alkyl sulfonic acids, ($C_6$-$C_{30}$)alkylamide sulfonic acids, ($C_6$-$C_{30}$)alkylaryl sulfonic acids, α-olefin sulfonic acids, paraffin sulfonic acids, ($C_6$-$C_{30}$) alkyl sulfosuccinic acids, ($C_6$-$C_{30}$) alkyl ether sulfosuccinic acids, ($C_6$-$C_{30}$) alkylamido sulfosuccinic acids, ($C_6$-$C_{30}$)alkyl sulfoacetic acids, ($C_6$-$C_{30}$)alkylpolyglycoside sulfosuccinic acids, ($C_6$-$C_{24}$)alkyl isethionic acids, N-[($C_6$-$C_{24}$)acyl] tauric acids, The sulfuric acid ester type surfactants, which may be used in the present invention, may include, but not limited to, ($C_6$-$C_{30}$)alkyl sulfuric acids, ($C_6$-$C_{30}$) alkyl ether sulfuric acids, ($C_6$-$C_{30}$)alkylamido ether sulfuric acids, alkylaryl polyether sulfuric acids, and monoglyceride sulfuric acids.

According to one embodiment of the present invention, the amount of the non-neutralized anionic surfactant(s) may range from 0.01 to 20% by weight, preferably 0.05 to 10% by weight, more preferably from 0.1 to 7% by weight relative to the total weight of the composition according to the present invention.

(b) Non-Ionic Surfactant

The composition comprises at least one nonionic surfactant. Two or more nonionic surfactants may be used in combination.

The nonionic surfactants are compounds well known in themselves (see, e.g., in this regard, "Handbook of Surfactants" by M. R. Porter, Blackie & Son publishers (Glasgow and London), 1991, pp. 116-178). Thus, they can, for example, be chosen from alcohols, alpha-diols, alkylphenols and esters of fatty acids, these compounds being ethoxylated, propoxylated or glycerolated and having at least one fatty chain comprising, for example, from 8 to 30 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils of plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$) alkylamine oxides or N—($C_{10}$-$C_{14}$) acylaminopropylmorpholine oxides; silicone surfactants; and mixtures thereof.

The nonionic surfactants may preferably be chosen from monooxyalkylenated, polyoxyalkylenated, monoglycerolated or polyglycerolated nonionic surfactants or mixtures thereof. The oxyalkylene units are more particularly oxyethylene or oxypropylene units, or a combination thereof, and are preferably oxyethylene units.

Examples of monooxyalkylenated or polyoxyalkylenated nonionic surfactants that may be mentioned include:

monooxyalkylenated or polyoxyalkylenated ($C_8$-$C_{24}$)alkylphenols, saturated or unsaturated, linear or branched, monooxyalkylenated or polyoxyalkylenated $C_8$-$C_{30}$ alcohols, saturated or unsaturated, linear or branched, monooxyalkylenated or polyoxyalkylenated $C_8$-$C_{30}$ amides, esters of saturated or unsaturated, linear or branched, $C_8$-$C_{30}$ acids and of polyalkylene glycols, monooxyalkylenated or polyoxyalkylenated esters of saturated or unsaturated, linear or branched, $C_8$-$C_{30}$ acids and of sorbitol, saturated or unsaturated, monooxyalkylenated or polyoxyalkylenated plant oils, condensates of ethylene oxide and/or of propylene oxide, inter alia, alone or as mixtures.

The surfactants preferably contain a number of moles of ethylene oxide and/or of propylene oxide of between 1 and 100 and most preferably between 2 and 50.

According to one of the embodiments of the present invention, the polyoxyalkylenated nonionic surfactants are chosen from polyoxyethylenated fatty alcohol (polyethylene glycol ether of fatty alcohol) and polyoxyethylenated fatty ester (polyethylene glycol ester of fatty acid).

Examples of polyoxyethylenated fatty alcohol (or $C_8$-$C_{30}$ alcohols) that may be mentioned include the adducts of ethylene oxide with lauryl alcohol, especially those containing from 9 to 50 oxyethylene units and more particularly those containing from 10 to 12 oxyethylene units (Laureth-10 to Laureth-12, as the CTFA names); the adducts of ethylene oxide with behenyl alcohol, especially those containing from 9 to 50 oxyethylene units (Beheneth-9 to Beheneth-50, as the CTFA names); the adducts of ethylene oxide with cetearyl alcohol (mixture of cetyl alcohol and stearyl alcohol), especially those containing from 10 to 30 oxyethylene units (Ceteareth-10 to Ceteareth-30, as the CTFA names); the adducts of ethylene oxide with cetyl alcohol, especially those containing from 10 to 30 oxyethylene units (Ceteth-10 to Ceteth-30, as the CTFA names); the adducts of ethylene oxide with stearyl alcohol, especially those containing from 2 to 30 oxyethylene units (Steareth-2 to Steareth-30, as the CTFA names); the adducts of ethylene oxide with isostearyl alcohol, especially those containing from 10 to 50 oxyethylene units (Isosteareth-10 to Isosteareth-50, as the CTFA names); and mixtures thereof.

As examples of the polyoxyalkylenated fatty alcohol containing 2 to 50 moles of propylene oxides, mention may be made of PPG-15 stearyl ether.

As examples of monoglycerolated or polyglycerolated nonionic surfactants, monoglycerolated or polyglycerolated $C_8$-$C_{40}$ alcohols are preferably used.

In particular, the monoglycerolated or polyglycerolated $C_8$-$C_{40}$ alcohols correspond to the following formula:

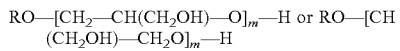

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the present invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

Among the monoglycerolated or polyglycerolated alcohols, it is preferable to use the $C_8/C_{10}$ alcohol containing 1 mol of glycerol, the $C_{10}/C_{12}$ alcohol containing 1 mol of glycerol and the $C_{12}$ alcohol containing 1.5 mol of glycerol.

The monoglycerolated or polyglycerolated $C_8$-$C_{40}$ fatty esters may correspond to the following formula:

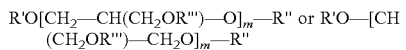

in which each of R', R" and R'" independently represents a hydrogen atom, or a linear or branched $C_8$-$C_{40}$ and preferably $C_8$-$C_{30}$ alkyl-CO— or alkenyl-CO-radical, with the proviso that at least one of R', R" and R'" is not a hydrogen atom, and m represents a number ranging from 1 to 30 and preferably from 1.5 to 10.

Examples of polyoxyethylenated fatty esters that may be mentioned include the adducts of ethylene oxide with esters of lauric acid, palmitic acid, stearic acid or behenic acid, and mixtures thereof, especially those containing from 9 to 100 oxyethylene units, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and polyoxyalkylenated derivatives thereof, preferably containing from 10 to 200, and more preferably from 10 to 100 oxyalkylene units, such as glyceryl esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sorbitol esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; sugar (sucrose, maltose, glucose, fructose, and/or alkylglycose) esters of a $C_8$-$C_{24}$, preferably $C_{12}$-$C_{22}$, fatty acid or acids and polyoxyalkylenated derivatives thereof, preferably containing from 10 to 200, and more preferably from 10 to 100 oxyalkylene units; ethers of fatty alcohols; ethers of sugar and a $C_8$-$C_{24}$, preferably $C_{12}$-$C_{22}$, fatty alcohol or alcohols; and mixtures thereof.

As glyceryl esters of fatty acids, glyceryl stearate (glyceryl mono-, di- and/or tristearate) (CTFA name: glyceryl stearate) or glyceryl ricinoleate and mixtures thereof can be cited, and as polyoxyalkylenated derivatives thereof, mono-, di- or triester of fatty acids with a polyoxyalkylenated glycerol (mono-, di- or triester of fatty acids with a polyalkylene glycol ether of glycerol), preferably polyoxyethylenated glyceryl stearate (mono-, di- and/or tristearate), such as PEG-20 glyceryl stearate (mono-, di- and/or tristearate) can be cited.

Mixtures of these surfactants, such as for example the product containing glyceryl stearate and PEG-100 stearate, marketed under the name ARLACEL 165 by Uniqema, and the product containing glyceryl stearate (glyceryl mono- and distearate) and potassium stearate marketed under the name TEGIN by Goldschmidt (CTFA name: glyceryl stearate SE), can also be used.

The sorbitol esters of $C_8$-$C_{24}$ fatty acids and polyoxyalkylenated derivatives thereof can be selected from sorbitan palmitate, sorbitan isostearate, sorbitan trioleate and esters of fatty acids and alkoxylated sorbitan containing for example from 20 to 100 EO, such as for example sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65, polyethylene sorbitan trioleate (polysorbate 85) or the compounds marketed under the trade names Tween 20 or Tween 60 by Uniqema.

As esters of fatty acids and glucose or alkylglucose, glucose palmitate, alkylglucose sesquistearates such as methylglucose sesquistearate, alkylglucose palmitates such as methylglucose or ethylglucose palmitate, methylglucoside fatty esters, the diester of methylglucoside and oleic acid (CTFA name: Methyl glucose dioleate), the mixed ester of methylglucoside and the mixture of oleic acid/hydroxystearic acid (CTFA name: Methyl glucose dioleate/hydroxystearate), the ester of methylglucoside and isostearic acid (CTFA name: Methyl glucose isostearate), the ester of methylglucoside and lauric acid (CTFA name: Methyl glucose laurate), the mixture of monoester and diester of methylglucoside and isostearic acid (CTFA name: Methyl glucose sesqui-isostearate), the mixture of monoester and diester of methylglucoside and stearic acid (CTFA name: Methyl glucose sesquistearate) and in particular the product marketed under the name Glucate SS by AMERCHOL, and mixtures thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (CTFA name: PEG-20 methyl glucose distearate) such as the product marketed under the name Glucam E-20 distearate by AMERCHOL, the polyethylene glycol ether of the mixture of monoester and diester of methyl-glucose and stearic acid with about 20 moles of ethylene oxide (CTFA name: PEG-20 methyl glucose sesquistearate) and in particular the product marketed under the name Glucamate SSE-20 by AMERCHOL and that marketed under the name Grillocose PSE-20 by GOLDSCHMIDT, and mixtures thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLANTAREN 2000 by Henkel, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by Henkel, coco-glucoside such as the product marketed under the name PLANTACARE 818/UP by Henkel, cetostearyl glucoside possibly mixed with cetostearyl alcohol, marketed for example under the name MONTANOV 68 by Seppic, under the name TEGO-CARE CG90 by Goldschmidt and under the name EMULGADE KE3302 by Henkel, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and mixtures thereof can in particular be cited.

Mixtures of glycerides of alkoxylated plant oils such as mixtures of ethoxylated (200 EO) palm and copra (7 EO) glycerides can also be cited.

The nonionic surfactant according to the present invention preferably contains alkenyl or branched $C_{12}$-$C_{22}$ acyl chain such as oleyl or isostearyl group. More preferably, the nonionic surfactant according to the present invention is PEG-20 glyceryl triisostearate.

According to one of the embodiments according to the present invention, the nonionic surfactant may be selected from copolymers of ethylene oxide and of propylene oxide, in particular copolymers of the following formula:

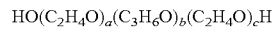

$$HO(C_2H_4O)_a(C_3H_6O)_b(C_2H_4O)_cH$$

in which a, b and c are integers such that a+c ranges from 2 to 100 and b ranges from 14 to 60, and mixtures thereof.

According to one of the embodiments according to the present invention, the nonionic surfactant may be selected from silicone surfactants. Non-limiting mention may be made of those disclosed in documents U.S. Pat. Nos. 5,364,633 and 5,411,744.

The silicone surfactant may preferably be a compound of formula (I):

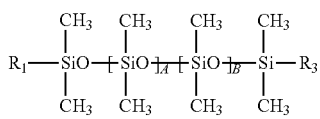

in which:

$R_1$, $R_2$ and $R_3$, independently of each other, represent a $C_1$-$C_6$ alkyl radical or a radical —$(CH_2)_x$—$(OCH_2CH_2)_y$—$(OCH_2CH_2)_z$—$OR_4$, at least one radical $R_1$, $R_2$ or $R_3$ not being an alkyl radical; $R_4$ being a hydrogen, an alkyl radical or an acyl radical;

A is an integer ranging from 0 to 200;

B is an integer ranging from 0 to 50; with the proviso that A and

B are not simultaneously equal to zero;

x is an integer ranging from 1 to 6;

y is an integer ranging from 1 to 30;

z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

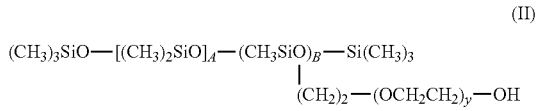

in which A is an integer ranging from 20 to 105, B is an integer ranging from 2 to 10 and y is an integer ranging from 10 to 20.

As examples of silicone surfactants of formula (I), mention may also be made of the compounds of formula (III):

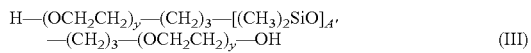

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The HLB of the nonionic surfactant(s) is preferably from 8 to 13, more preferably 9 to 12, and even more preferably 10 to 11. If two or more nonionic surfactants are used, the HLB value is determined by the weight average of the HLB values of all the nonionic surfactants. The HLB is the ratio between the hydrophilic part and the lipophilic part in the molecule. This term HLB is well known to those skilled in the art and is described in "The HLB system. A time-saving guide to emulsifier selection" (published by ICI Americas Inc., 1984). If the HLB of the nonionic surfactant(s) is lower than 8, the oily feeling after rinsing-off would remain. If the HLB of the nonionic surfactant(s) is higher than 13, the removability of the composition would be worse.

According to one embodiment of the present invention, the amount of the non-ionic surfactant(s) may range from 0.1 to 20% by weight, preferably from 0.5 to 10% by weight, more preferably 1 to 7% by weight relative to the total weight of the composition according to the present invention.

(c) Fatty Alcohol

The term "fatty" here means the inclusion of a relatively large number of carbon atoms. Thus, alcohols which have 6 or more, preferably 8 or more, and more preferably 10 or more carbon atoms are encompassed within the scope of fatty alcohols. The fatty alcohols may be saturated or unsaturated. The fatty alcohol may be linear or branched. Two or fatty alcohols may be used in combination.

The fatty alcohol may have the structure R—OH wherein R is chosen from saturated and unsaturated, linear and branched radicals containing from 8 to 40 carbon atoms, for example from 8 to 30 carbon atoms. In at least one embodiment, R is chosen from $C_{12}$-$C_{24}$ alkyl and $C_{12}$-$C_{24}$ alkenyl groups. R may be or may not be substituted with at least one hydroxyl group.

Non-limiting examples of fatty alcohols that may be mentioned include lauryl alcohol, cetyl alcohol, stearyl alcohol, oleyl alcohol, behenyl alcohol, linoleyl alcohol, undecylenyl alcohol, palmitoleyl alcohol, arachidonyl alcohol, erucyl alcohol, cetearyl alcohol, and mixtures thereof.

Examples of suitable fatty alcohols include, but are not limited to, cetyl alcohol, cetearyl alcohol, stearyl alcohol, behenyl alcohol, oleyl alcohol, and mixtures thereof.

The fatty alcohol may represent a mixture of fatty alcohols, which means that several species of fatty alcohol may coexist, in the form of a mixture, in a commercial product.

According to at least one embodiment, the fatty alcohol used in the composition according to the present invention is chosen from cetyl alcohol and cetearyl alcohol.

According to one embodiment of the present invention, the amount of the fatty alcohol may range from 0.1 to 40% by weight, preferably from 0.5 to 30% by weight, and more preferably from 1 to 20% by weight, relative to the total weight of the composition according to the present invention.

(d) Alkaline Agent

The alkaline agent may be an inorganic alkaline agent. It is preferable that the inorganic alkaline agent be selected from the group consisting of ammonia; alkaline metal hydroxides; alkaline earth metal hydroxides; alkaline metal phosphates and monohydrogenophosphates such as sodium phosphate or sodium monohydrogeno phosphate; ammonium hydroxide; and ammonium bicarbonate. Two or more alkaline agents may be used.

As examples of the alkaline metal hydroxides, mention may be made of sodium hydroxide and potassium hydroxide. As examples of the alkaline earth metal hydroxides, mention may be made of calcium hydroxide and magnesium hydroxide. As the inorganic alkaline agent, sodium hydroxide, ammonium hydroxide, ammonia, and ammonium bicarbonate are preferable.

The alkaline agent may be an organic alkaline agent. It is preferable that the organic alkaline agent be selected from the group consisting of monoamines and derivatives thereof; diamines and derivatives thereof; polyamines and derivatives thereof; basic amino acids and derivatives thereof; oligomers of basic amino acids and derivatives thereof;

polymers of basic amino acids and derivatives thereof; urea and derivatives thereof; and guanidine and derivatives thereof.

As examples of the organic alkaline agents, mention may be made of alkanolamines such as mono-, di- and tri-ethanolamine, and isopropanolamine; urea, guanidine and their derivatives; basic amino acids such as lysine, ornithine or arginine; and diamines such as those described in the structure below:

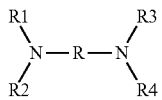

wherein

R denotes an alkylene such as propylene optionally substituted by a hydroxyl or a $C_1$-$C_4$ alkyl radical, and $R_1$, $R_2$, $R_3$ and $R_4$ independently denote a hydrogen atom, an alkyl radical, or a $C_1$-$C_4$ hydroxyalkyl radical, which may be exemplified by 1,3-propanediamine and derivatives thereof. Arginine, urea, and monoethanolamine are preferable.

Preferably, the alkaline agent includes ammonia due to its safety and performance, such as hair coloring performance and hair permanent waving performance. Another alkaline agent may be mixed with ammonia.

The alkaline agent can change the pH value of the mixture to alkaline pH. The pH value of the obtained composition according to the present invention is generally, for example, from 7 to 12, preferably from 8 to 11, more preferably from 9 to 11.

According to one embodiment of the present invention, the amount of the alkaline agent(s) may range from 0.01 to 20% by weight, preferably 0.05 to 10% by weight, more preferably from 0.1 to 7% by weight relative to the total weight of the composition according to the present invention.

(e) Other Components

The composition according to present invention may comprise other components usually used in cosmetic compositions for keratin fibers, in particular hair dyeing agent for coloring keratin fibers or hair permanent waving agent for reshaping keratin fibers. The other components may include, but not limited to, oils, water, oxidation dyes, direct dyes, reducing agents, and various adjuvants.

The term "oil" here means an organic compound that is insoluble in water at ordinary temperature (25° C.) and at atmospheric pressure (760 mmHg) (solubility of less than 5%, preferably 1% and even more preferentially 0.1%). In addition, the oils are soluble in organic solvents under the same temperature and pressure conditions, for instance chloroform, ethanol or benzene. More particularly, the oil is chosen from compounds that are liquid or pasty at room temperature and at atmospheric pressure. Preferably, the oil is a compound that is liquid at a temperature of 25° C.) and at atmospheriC pressure. For the purposes of the invention, the term "oil" does not include fatty acids.

Examples of oils that may be used include non-silicone fatty substances such as alkanes, fatty alcohols, fatty acid esters, fatty alcohol esters, liquid paraffin, mineral oils, plant oils, animal oils, synthetic oils, non-silicone waxes, and silicones.

The amount of the oil(s) may be 0.1 to 30% by weight, preferably 2 to 25% by weight relative to the total weight of the composition according to the present invention.

The oxidation dyes are generally chosen from one or more oxidation bases optionally combined with one or more couplers.

For example, the oxidation bases are chosen from para-phenylenediamines, bis(phenyl)alkylenediamines, para-aminophenols, ortho-aminophenols, and heterocyclic bases, such as, pyridine derivatives, pyrimidine derivatives, and pyrazole derivatives, and addition salts thereof. The couplers which can be used include, but not limited to, meta-phenylenediamines, meta-aminophenols, meta-diphenols, resorcinol, 2-methyl-5-hydroxyethylaminophenol, 4-amino-2-hydroxytoluene, naphthalene-based couplers and heterocyclic couplers, and also the addition salts thereof.

The amount of the oxidation dye(s) may be 0.0001 to 10% by weight, preferably 0.005 to 5% by weight relative to the total weight of the composition. The content of coupler(s), if it is (they are) present, advantageously represents from 0.0001% to 10% by weight, preferably from 0.005% to 5% by weight relative to the total weight of the composition according to the present invention.

The direct dyes which can be used in the composition according to the present invention may include nitrobenzene dyes, azo direct dyes, and methane direct dyes. These direct dyes can be non-ionic, anionic, or cationic in nature. The direct dye may be used in combination.

The amount of the direct dye(s) may be 0.0005 to 12% by weight, preferably 0.005 to 6% by weight relative to the total weight of the composition according to the present invention.

The reducing agents which can be used in the composition according to the present invention may include sulfured compounds, such as thiols, sufites and hydrosulfites, and non-sulfured compounds such as reductones, in particular ascorbic acids and erythorbic acids and their salts.

The one or more reducing agents, if which are present, may be from 0.0005% to 20% by weight, preferably from 0.05% to 10% by weight relative to the total weight of the composition according to the present invention.

The adjuvants may be adjuvants conventionally used in hair cosmetic composition. Examples of the adjuvants include anionic, cationic, non-ionic, amphoteric or zwitterionic copolymers, or mixtures thereof; mineral thickeners, and in particular fillers such as clays, talcs; organic thickeners with, in particular, anionic, cationic, non-ionic, and amphoteric polymeric associative thickeners; penetrants; ionic surfactants, such as cationic, anionic, zwitterionic surfactants; sequestrants, such as EDTA and pentasodium pentetate; fragrances; dispersants; film-forming agents; ceramides; preserving agents; antioxidants, such as sodium metabisulfite; opacifiers; and polyols, such as sorbitol and PEG-20.

Each of the above adjuvants is generally present in an amount of between 0.01% and 20% by weight relative to the weight of the composition according to the present invention.

The present invention also relates to a composition for keratin fibers having 3 Pas or more of viscosity at 25° C. The viscosity can be measured by well-known methods, for example, using Rheomat 180 viscometer (Rheometric Scientific).

In one embodiment, the composition according to the present invention is in a form of an emulsion. The emulsion may comprise an oil phase comprising the (a) non-neutralized anionic surfactant, the (b) non-ionic surfactant, and the (c) fatty alcohol, and an aqueous phase. Advantageously, the composition according to the present invention is in the form of a gel or a cream.

The aqueous phase in the emulsion can be composed essentially of water or can comprise a mixture of water and of water miscible solvent chosen from, for example, monoalcohols having from 1 to 5 carbon atoms, such as ethanol or isopropanol, glycols having from 2 to 8 carbon atoms, such as propylene glycol, ethylene glycol, 1,3-butylene glycol or dipropylene glycol, $C_3$-$C_4$ ketones, $C_2$-$C_4$ aldehydes and mixtures thereof.

According to this embodiment of the present invention, the amount of the aqueous phase may range from 1 to 90% by weight, preferably from 2 to 85% by weight, and more preferably from 3 to 80% by weight, relative to the total weight of the composition according to the present invention.

The pH value of the composition according to the present invention is generally, for example, from 6 to 12. It can range from 7 to 11, preferably from 8 to 11, more preferably from 9 to 11.

The mechanism enabling the composition according to the present invention to reduce its ammonia odor is not very clear at this time. However, it is assumed that the present invention produces an effect of trapping the alkaline agents in the composition. Specifically, the composition before the addition of alkaline agents may be in an emulsion form consisting of a lamellar structure, and after the addition of alkaline agents, it is assumed that the alkaline agents and water can be deeply immersed between lamellar structures. Consequently, it is assumed that the alkaline agents may be trapped between the lamellar structures.

The composition can be used for cosmetic treatment for keratin fibers such as hair. For example, the composition according to the present invention can be used for coloring keratin fibers or reshaping keratin fibers.

The composition according to the present invention can suppress its offensive ammonia odor. Specifically, this composition can suppress offensive ammonia odor which may generate when this composition is mixed with an oxidation hair dye or a hair bleaching agent (i.e. a developer).

When the composition is used in order to dye keratin fibers, the coloring process for keratin fibers can be performed by, first, mixing the composition according to the present invention with a developer comprising one or more oxidizing agents. The mixing ratio of the composition according to the present invention and the developer may be 1:1 to 1:3, preferably 1:1 to 1:2.5.

More particularly, the oxidizing agent(s) is (are) chosen from the group consisting of hydrogen peroxide, urea peroxide, alkali metal bromates or ferricyanides, and peroxygenated salts, for instance alkali metal or alkaline-earth metal persulfates, perborates and percarbonates, and peracids and precursors thereof.

The oxidizing agent is advantageously constituted by hydrogen peroxide, especially as an aqueous solution (aqueous hydrogen peroxide solution), the concentration of which may range from 1 to 50% by weight and preferably from 5 to 40% by weight.

As a function of the desired degree of lightening, the developer may also comprise an oxidizing agent preferably chosen from peroxygenated salts.

The developer may be aqueous or non-aqueous. The term "aqueous" means that the developer comprises more than 5% by weight of water, preferably more than 10% by weight of water and even more advantageously more than 20% by weight of water.

Usually, the pH of the developer, when it is aqueous, is less than 7.

The developer may also contain other ingredients conventionally used in the field, especially those detailed previously in the context of the composition according to the present invention.

The developer is in various forms, for instance a solution, an emulsion or a gel.

Next, the mixture of the composition according to the present invention and the developer is applied onto keratin fibers such as hair, and washed out after appropriate processing time. As a result, the keratin fibers such as hair can be colored or breached.

On the other hand, the composition for reshaping keratin fibers according to the present invention typically contains a reducing agent, such as thioglycolic acid, for breaking a disulfide bond in the keratin fibers. The composition for reshaping keratin fibers according to the present invention may also contain various adjuvants as mentioned above. Each of the above adjuvants are generally present in an amount of between 0.01% and 20% by weight relative to the weight of the composition according to the present invention.

The reshaping process for keratin fibers according to the present invention may be performed as follows.

First, keratin fibers are subjected to mechanical tension for deformation. The mechanical tension can be applied to the keratin fibers by any means to deform the keratin fibers to an intended shape. For example, the mechanical tension may be provided by at least one reshaping means selected from the group consisting of a curler, a roller, a plate, and an iron. The reshaping means may comprise at least one heater.

Next, the composition for reshaping keratin fibers according to the present invention is applied to the keratin fibers. Thus, a disulfide bond in the keratin fibers is broken. The application of the composition may be performed by any means, such as a brush and a comb. The keratin fibers to which the mechanical tension has been applied should be treated with the composition.

Next, an oxidizing composition comprising one or more oxidizing agents as described above is applied onto the keratin fibers to form a disulfide bond again. As a result, the keratin fibers such as hair can be reshaped.

The keratin fibers may be rinsed after the step of applying the cosmetic composition according to the present invention onto the keratin fibers and/or after the step of heating the keratin fibers.

If necessary, the composition according to the present invention may be applied to keratin fibers before and/or during the application of mechanical tension to the keratin fibers.

(II) Method for Preparing the Composition

Another aspect of the present invention relates to a method for preparing a composition for keratin fibers, such as hair, comprising the steps of (i) mixing (a) at least one non-neutralized anionic surfactant, (b) at least one non-ionic surfactant and (c) at least one fatty alcohol to prepare an oil phase, (ii) mixing the oil phase obtained in step (i) with an aqueous phase to prepare an emulsion, and (iii) adding (d) at least one alkaline agent to the emulsion obtained in step (ii).

The method according to the present invention is a method for preparing the composition according to the present invention. In general, the composition is prepared by mixing (a) at least one non-neutralized anionic surfactant, (b) at least one non-ionic surfactant, (c) at least one fatty alcohol; and (d) at least one alkaline agent. Preferably, components (a) to (c) are mixed first, and then component (d) is mixed.

According to the method of the present invention, it can produce the composition for keratin fibers, such as hair, in which the ammonia odor is reduced. Furthermore, it was surprisingly found that the method according to the present invention could produce the composition having improved stability with its increased viscosity. Therefore, the obtained composition is easy to mix and to apply, and will especially not run but remain localized at the point of application.

Step (i) is a step to mix (a) at least one non-neutralized anionic surfactant, (b) at least one non-ionic surfactant and (c) at least one fatty alcohol to prepare an oil phase.

The temperature during step (i) is not limited, however, preferably step (i) can be carried out at a temperature from 40 to 95° C., preferably from 50 to 85° C.

Step (ii) is a step to mix the oil phase obtained in step (i) with an aqueous phase to prepare an emulsion.

The temperature during step (ii) is not limited, however, preferably, step (ii) can be carried out at a temperature from 40 to 95° C., preferably from 50 to 85° C.

The pH value of the emulsion in the step (ii) may be below 9.5, preferably below 9.0, more preferably below 8.0, and even more preferably below 7.0, and the most preferably below 7.0.

Step (iii) is a step to add (d) at least one alkaline agent to the emulsion obtained in step (ii).

The temperature during step (iii) is not limited, however, preferably step (iii) can be carried out at a temperature more than 0 to 40° C., preferably from 10 to 30° C.

Other components other than components (a) to (d) can be added accordingly before, during, or after steps (i) to (iii). For example, other components which can disperse, dissolve, or be miscible in the oil phase, such as oils, copolymers, and organic thickeners, can be added to the oil phase during Step (i). Other components which can disperse, dissolve, or be miscible in the aqueous phase can be added with the aqueous phase in Step (ii). Among other components, in particular heat sensitive ingredients may be added to the emulsion at a temperature more than 0 to 40° C. when the alkaline agents are added.

The mechanism which enables the method according to the present invention to produce a stable composition is not very clear at this time. However, in the same manner as the mechanism of alkaline agent-trapping effect of the composition according to the present invention as described above, it can be assumed that an immersion of alkaline agents between lamella structures of the emulsion can produce structured continuous phase of the composition. And thus, it can be assumed that the method according to the present invention can produce the stable composition with increased viscosity.

EXAMPLES

The present invention will be described in more detail by way of examples, which however should not be construed as limiting the scope of the present invention.

(I) Comparison in Sniff Test and Viscosity

The compositions in accordance with Examples 1 to 8 and Comparative Examples 1 to 4 were prepared by mixing the components shown in Tables 1 to 3. In the examples, the numerical values for the amounts of the components shown in Tables are all based on "% by weight".

[Preparation Protocol]

(i) (a) the non-neutralized anionic surfactant (inventive) or (a') the neutralized anionic surfactant (comparative), (b) the non-ionic surfactants, (c) the fatty alcohol, and mineral oil were mixed at 80° C. to prepare an oil phase (ii) the oil phase obtained in step (i) was mixed with water, sorbitol, pentasodium pentetate, erythorbic acid, sodium metabisulfite, p-phenylenediamine, p-aminophenol, resorcinol, m-aminophenol, 2-methyl-5-hydroxyethylaminophenol, and 4-amino-2-hydroxytoluene at 80° C. to prepare an emulsion (iii) (d) alkaline agent and perfume were added to the emulsion obtained in step (ii) and the obtained mixture was mixed at room temperature (25° C.)

The following ingredients were used in the examples.
(a) Laureth-5 Carboxylic Acid (Akypo RLM 45. CA, Kao)
(a) Cocoyl Glutamic Acid (Aminosurfact CCA, Asahi Kasei Chemicals)
(a) Lauroyl Methyl Beta-Alanine (Alanon ALA, Kawaken Fine Chemicals)
(a) Myristoyl Methyl Beta-Alanine (Alanon AMA, Kawaken Fine Chemicals)
(a) Cocoyl Sarcosine (Soypon SCA, Kawaken Fine Chemicals)
(b) Steareth-2 (Brij S2, Croda)
(b) Steareth-2 (Brij S20, Croda)
(b) Ceteth-10 (Brij C10, Croda)
(b) PPG-15 stearyl ether (Arlamol PS15E-LQ-(RB), Croda)

TABLE 1

| Type | Ingredient Name | Example 1 | Example 2 | Example 3 | Example 4 |
|---|---|---|---|---|---|
| (b) | Steareth-2 | 1.5 | 1.5 | 1.5 | 1.5 |
| (b) | Steareth-20 | 1 | 1 | 1 | 1 |
| (b) | Ceteth-10 | 0.7 | 0.7 | 0.7 | 0.7 |
| (b) | PPG-15 stearyl ether | 1.5 | 1.5 | 1.5 | 1.5 |
| (c) | Cetearyl Alcohol | 16 | 16 | 16 | 16 |
|  | Mineral Oil | 2 | 2 | 2 | 2 |
| (a) | Stearic Acid | 0.3 | — | — | — |
| (a) | Oleic Acid | — | 0.3 | — | — |
| (a) | Lauric Acid | — | — | 0.3 | — |
| (a) | Cocoyl Glutamic Acid | — | — | — | 0.3 |
|  | Sorbitol | 4 | 4 | 4 | 4 |
|  | Pentasodium Pentetate (40%) | 0.2 | 0.2 | 0.2 | 0.2 |
|  | Erythorbic Acid | 0.5 | 0.5 | 0.5 | 0.5 |
|  | Sodium Metabisulfite | 0.5 | 0.5 | 0.5 | 0.5 |
|  | p-Phenylenediamine | 0.5 | 0.5 | 0.5 | 0.5 |
|  | p-Aminophenol | 0.16 | 0.16 | 0.16 | 0.16 |
|  | Resorcinol | 0.5 | 0.5 | 0.5 | 0.5 |
|  | m-Aminophenol | 0.11 | 0.11 | 0.11 | 0.11 |
|  | 2-Methyl-5-hydroxyethylaminophenol | 0.1 | 0.1 | 0.1 | 0.1 |
|  | 4-Amino-2-hydroxytoluene | 0.03 | 0.03 | 0.03 | 0.03 |
|  | Perfume | 0.4 | 0.4 | 0.4 | 0.4 |
| (d) | Ammonia (20%) | 8.8 | 8.8 | 8.8 | 8.8 |
|  | Water | qs. | qs. | qs. | qs. |

TABLE 2

| Type | Ingredient Name | Example 5 | Example 6 | Example 7 | Example 8 |
|---|---|---|---|---|---|
| (b) | Steareth-2 | 1.5 | 1.5 | 1.5 | 1.5 |
| (b) | Steareth-20 | 1 | 1 | 1 | 1 |
| (b) | Ceteth-10 | 0.7 | 0.7 | 0.7 | 0.7 |
| (b) | PPG-15 stearyl ether | 1.5 | 1.5 | 1.5 | 1.5 |
| (c) | Cetearyl Alcohol | 16 | 16 | 16 | 16 |
|  | Mineral Oil | 2 | 2 | 2 | 2 |
| (a) | Lauroyl Methyl Beta-Alanine | 0.3 | — | — | — |
| (a) | Myristoyl Methyl Beta-Alanine | — | 0.3 | — | — |
| (a) | Cocoyl Sarcosine | — | — | 0.3 | — |
| (a) | Laureth-5 Carboxylic Acid (90%) | — | — | — | 0.33 |

TABLE 2-continued

| Type | Ingredient Name | Example 5 | 6 | 7 | 8 |
|---|---|---|---|---|---|
| | Sorbitol | 4 | 4 | 4 | 4 |
| | Pentasodium Pentetate (40%) | 0.2 | 0.2 | 0.2 | 0.2 |
| | Erythorbic Acid | 0.5 | 0.5 | 0.5 | 0.5 |
| | Sodium Metabisulfite | 0.5 | 0.5 | 0.5 | 0.5 |
| | p-Phenylenediamine | 0.5 | 0.5 | 0.5 | 0.5 |
| | p-Aminophenol | 0.16 | 0.16 | 0.16 | 0.16 |
| | Resorcinol | 0.5 | 0.5 | 0.5 | 0.5 |
| | m-Aminophenol | 0.11 | 0.11 | 0.11 | 0.11 |
| | 2-Methyl-5-hydroxyethylaminophenol | 0.1 | 0.1 | 0.1 | 0.1 |
| | 4-Amino-2-hydroxytoluene | 0.03 | 0.03 | 0.03 | 0.03 |
| | Perfume | 0.4 | 0.4 | 0.4 | 0.4 |
| (d) | Ammonia (20%) | 8.8 | 8.8 | 8.8 | 8.8 |
| | Water | qs. | qs. | qs. | qs. |

TABLE 3

| Type | Ingredient Name | Comparative Example 1 | 2 | 3 | 4 |
|---|---|---|---|---|---|
| (b) | Steareth-2 | 1.5 | 1.5 | 1.5 | 1.5 |
| (b) | Steareth-20 | 1 | 1 | 1 | 1 |
| (b) | Ceteth-10 | 0.7 | 0.7 | 0.7 | 0.7 |
| (b) | PPG-15 stearyl ether | 1.5 | 1.5 | 1.5 | 1.5 |
| (c) | Cetearyl Alcohol | 16 | 16 | 16 | 16 |
| | Mineral Oil | 2 | 2 | 2 | 2 |
| (a') | Sodium Cetearyl Sulfate (96%) | — | 0.3 | — | — |
| (a') | Disodium Stearoyl Glutamate | — | — | 0.3 | — |
| (a') | Behentrimonium Chloride (79%) | — | — | — | 0.38 |
| | Sorbitol | 4 | 4 | 4 | 4 |
| | Pentasodium Pentetate (40%) | 0.2 | 0.2 | 0.2 | 0.2 |
| | Erythorbic Acid | 0.5 | 0.5 | 0.5 | 0.5 |
| | Sodium Metabisulfite | 0.5 | 0.5 | 0.5 | 0.5 |
| | p-Phenylenediamine | 0.5 | 0.5 | 0.5 | 0.5 |
| | P-Aminophenol | 0.16 | 0.16 | 0.16 | 0.16 |
| | Resorcinol | 0.5 | 0.5 | 0.5 | 0.5 |
| | m-Aminophenol | 0.11 | 0.11 | 0.11 | 0.11 |
| | 2-Methyl-5-hydroxyethylaminophenol | 0.1 | 0.1 | 0.1 | 0.1 |
| | 4-Amino-2-hydroxytoluene | 0.03 | 0.03 | 0.03 | 0.03 |
| | Perfume | 0.4 | 0.4 | 0.4 | 0.4 |
| (d) | Ammonia (20%) | 8.8 | 8.8 | 8.8 | 8.8 |
| | Water | qs. | qs. | qs. | qs. |

[Evaluations]

For each composition of Examples 1 to 8 and Comparative Examples 1 to 4, the evaporation of ammonia was evaluated by Sniff test and the stability of the composition was evaluated by its viscosity as follows.

(Sniff Test)

Each obtained composition of Examples 1 to 8 and Comparative Examples 1 to 4 was mixed with developer A composition in 1:1 weight ratio. The constituents of developer A are shown in Table 4.

TABLE 4

| Ingredient Name | Developer A |
|---|---|
| Mineral Oil | 0.8 |
| Stearyl Alcohol | 0.7 |
| Cetyl Alcohol | 0.7 |
| Myristyl Alcohol | 2.8 |
| Ceteareth-33 | 1.7 |
| Beheneth-10 | 0.5 |
| Cocamidopropyl Betaine (30%) | 0.143 |
| Polyquaternium-6 | 0.5 |
| Tetrasodium Etidronate (30%) | 0.2 |
| Tetrasodium Pyrophosphate | 0.04 |
| Sodium Salicylate | 0.035 |
| Hydrogen Peroxide (50%) | 11.7 |
| Phosphoric Acid | qs to pH 2.2 |
| Water | qs to 100 |

5 panels conducted sensory evaluation by directly sniffing the mixture, and scored in accordance with the following criteria.

1: Ammonia odor was very weak
2: Ammonia odor was weak
3: Ammonia odor was medium
4: Ammonia odor was strong
5: Ammonia odor was very strong (Viscosity)

The viscosity of the each obtained composition of Examples 1 to 8 and Comparative Examples 1 to 4 itself was measured by using Rheomat 180 viscometer (Rheometric Scientific) with No. 4 spindle at 200 rpm at 25° C. The measurement of the viscosity was carried out after 30 seconds from the time when the spindle rotation started, and a thickening was scored in accordance with the following criteria.

A: >7 Pas, Stable thickened composition
B: 3 to 7 Pas, Relatively stable thickened composition and no practical problem
C: <3 Pas, Not stable thickened composition The results of the evaluations are shown in Table 5.

TABLE 5

| Score (averaged) | Example | | | | | | | | Comparative Example | | | |
|---|---|---|---|---|---|---|---|---|---|---|---|---|
| | 1 | 2 | 3 | 4 | 5 | 6 | 7 | 8 | 1 | 2 | 3 | 4 |
| Sniff Test | 1 | 1 | 2 | 1 | 1 | 1 | 1 | 2 | 5 | 4 | 5 | 4 |
| Viscosity | A | A | B | A | A | A | A | A | C | C | C | B |

As shown in Table 5, Examples 1 to 8 comprising (a) non-neutralized anionic surfactants show substantially reduced or acceptable ammonia odor and improved stability with its increased viscosity. In contrast, Comparative Examples 1 to 3 lacking (a) non-neutralized anionic surfactants generate strong ammonia odor and does not show the stability. Comparative Example 4 also lacking the (a) non-neutralized anionic surfactants but including a cationic surfactant shows good viscosity, but generates uncomfortable ammonia odor in the same manner as Comparative Examples 1 to 3.

(II) Comparison with Chemi-Luminescence Test

The compositions in accordance with Example 9 and Comparative Example 5 were prepared by mixing the components shown in Table 6.

[Preparation Protocol]

(i) (a) the non-neutralized anionic surfactant (inventive) or (a') the phosphoric surfactant (comparative), (b) the non-ionic surfactants, (c) the fatty alcohol, and mineral oil were mixed at 80° C. to prepare an oil phase (ii) the oil phase obtained in step (i) was mixed with water, PEG-20, EDTA, ascorbic acid, sodium metabisulfite, and hexadimethrine chloride (only comparative) at 80° C. to prepare an emulsion (iii) (d) the alkaline agents was added to the emulsion obtained in step (ii) and the obtained mixture was mixed at room temperature (25° C.)

TABLE 6

| Type | Ingredient Name | Example 9 | Comparative Example 5 |
|---|---|---|---|
| (b) | Steareth-2 | 1.5 | 1.7 |
| (b) | Steareth-20 | 1 | 1.1 |
| (b) | Ceteth-10 | 0.7 | — |
| (b) | PPG-15 stearyl ether | 1.5 | 1.7 |
| (c) | Cetearyl Alcohol | 11 | 11 |
|  | Mineral Oil | 7 | 9 |
| (a) | Stearic Acid | 0.3 | — |
| (a') | Dicetyl Phosphate (and) Ceteth-10 Phosphate | — | 0.7 |
|  | PEG-20 | 4 | 4 |
| (d) | Ethanolamine | — | 0.28 |
|  | Hexadimethrine Chloride | — | 0.01 |
|  | EDTA | 0.2 | 0.2 |
|  | Ascorbic Acid | 0.5 | 0.5 |
|  | Sodium Metabisulfite | 0.5 | 0.5 |
| (d) | Ammonia (20%) | 9 | 9 |
| (d) | Ammonium Bicarbonate | 2 | 2 |
|  | Water | qs. | qs. |

[Evaluation]

For each composition of Example 9 and Comparative Example 5, the evaporation of ammonia was evaluated by the Chemi-Luminescence test as follows.

(Chemi-Luminescence Test)

Each obtained composition of Example 9 and Comparative Example 5 was mixed with a developer B composition in 1:1 weight ratio. The constituents of developer B are shown in Table 7.

TABLE 7

| Ingredient Name | Developer B |
|---|---|
| Mineral Oil | 0.8 |
| Cetearyl Alcohol | 5.5 |
| Ceteareth-33 | 1.7 |
| Beheneth-10 | 0.5 |
| Polyquaternium-6 | 0.5 |
| Tetrasodium Etidronate (30%) | 0.2 |
| Tetrasodium Pyrophosphate | 0.04 |
| Sodium Salicylate | 0.035 |
| Hydrogen Peroxide (50%) | 11.7 |
| Phosphoric Acid | qs to pH 2.2 |
| Water | qs to 100 |

The concentration of ammonia evaporated from the mixture was determined by using a chemi-luminescence detecting system (CLD 822 CMI by Eco Physics AG, Switzerland, N=5).

The result is shown in Table 8.

TABLE 8

|  | Example 9 | | Comparative Example 5 | |
|---|---|---|---|---|
|  | Average | σ | Average | σ |
| Maximum value of ammonia emitted | 151 | 6 | 209 | 19 |
| Total emission of ammonia during 10 minutes | 61448 | 2327 | 90185 | 7462 |

σ: Standard deviation

As shown in Table 8, Example 9 comprising (a) non-neutralized anionic surfactants regulates the emission of ammonia. In contrast, Comparative Example 5 comprising more than 0.2% of (a') phosphoric surfactants generates more ammonia than Example 9.

(III) Comparison in Manufacturing Process

The compositions according to the present invention produced from different manufacturing methods were compared based on the same constituents.

The components of the composition used in these examples are shown in Table 9.

TABLE 9

| Type | Ingredient Name | |
|---|---|---|
| (b) | Steareth-2 | 1.5 |
| (b) | Steareth-20 | 1 |
| (b) | Ceteth-10 | 0.7 |
| (b) | PPG-15 stearyl ether | 1.5 |
| (c) | Cetearyl Alcohol | 16 |
|  | Mineral Oil | 2 |
| (a) | Stearic Acid | 0.3 |
|  | Sorbitol | 4 |
|  | Pentasodium Pentetate (40%) | 0.2 |
|  | Erythorbic Acid | 0.5 |
|  | Sodium Metabisulfite | 0.5 |
|  | p-Phenylenediamine | 0.5 |
|  | p-Aminophenol | 0.16 |
|  | Resorcinol | 0.5 |
|  | m-Aminophenol | 0.11 |
|  | 2-Methyl-5-hydroxyethylaminophenol | 0.1 |
|  | 4-Amino-2-hydroxytoluene | 0.03 |
|  | Perfume | 0.4 |
| (d1) | Ethanolamine | 0.68 |
| (d2) | Ammonia (20%) | 8.8 |
|  | Water | qs. |

Manufacturing Example 1 was carried out according to the preparation protocol (i) below.

[Preparation Protocol (i)]

(i) (a) the non-neutralized-anionic-surfactant, (b) the non-ionic surfactants, (c) the fatty alcohol, and mineral oil were mixed at 80° C. to prepare an oil phase (ii) the oil phase obtained in step (i) was mixed with water, sorbitol, pentasodium pentetate, erythorbic acid, sodium metabisulfite, p-phenylenediamine, p-aminophenol, resorcinol, m-aminophenol, 2-methyl-5-hydroxyethylaminophenol, and 4-amino-2-hydroxytoluene at 80° C. to prepare an emulsion (iii) (d1) ethanol amine, (d2) ammonia, and perfume were added to the emulsion obtained in step (ii) and the obtained mixture was mixed at room temperature (25° C.)

Manufacturing Example 2 was carried out according to the preparation protocol (ii) below.

[Preparation Protocol (ii)]

(i) (a) the non-neutralized anionic surfactant, (b) the non-ionic surfactants, (c) the fatty alcohol, and mineral oil were mixed at 80° C. to prepare an oil phase (ii) the oil phase obtained in step (i) was mixed with water, (d1) ethanol amine, sorbitol, pentasodium pentetate, erythorbic acid, sodium metabisulfite, p-phenylenediamine, p-aminophenol, resorcinol, m-aminophenol, 2-methyl-5-hydroxyethylaminophenol, and 4-amino-2-hydroxytoluene at 80° C. to prepare an emulsion (iii) (d2) ammonia and perfume were added to the emulsion obtained in step (ii) and the obtained mixture was mixed at room temperature (25° C.)

[Evaluations]

Manufacturing Examples 1 and 2 were compared in the points of (1) the pH value of the emulsions obtained in step (ii) and compositions obtained in step (iii), (2) the viscosity of the emulsions and compositions, and (3) the evaporation of ammonia by Sniff test.

(Sniff Test)

Each obtained composition of Manufacturing Examples 1 and 2 was mixed with a developer A composition in 1:1 weight ratio. The constituents of the developer A are shown in Table 10.

TABLE 10

| Ingredient Name | Developer A |
| --- | --- |
| Mineral Oil | 0.8 |
| Stearyl Alcohol | 0.7 |
| Cetyl Alcohol | 0.7 |
| Myristyl Alcohol | 2.8 |
| Ceteareth-33 | 1.7 |
| Beheneth-10 | 0.5 |
| Cocamidopropyl Betaine (30%) | 0.143 |
| Polyquaternium-6 | 0.5 |
| Tetrasodium Etidronate (30%) | 0.2 |
| Tetrasodium Pyrophosphate | 0.04 |
| Sodium Salicylate | 0.035 |
| Hydrogen Peroxide (50%) | 11.7 |
| Phosphoric Acid | qs to pH 2.2 |
| Water | qs to 100 |

5 panels conducted sensory evaluation by directly sniffing the mixture, and scored in accordance with the following criteria.

1: Ammonia odor was very weak
2: Ammonia odor was weak
3: Ammonia odor was medium
4: Ammonia odor was strong
5: Ammonia odor was very strong
(Viscosity)

The viscosity of the each obtained composition of Manufacturing Examples 1 and 2 itself was measured by using Rheomat 180 viscometer (Rheometric Scientific) with No. 4 spindle at 200 rpm at 25° C. The measurement of the viscosity was carried out after 30 seconds from the time when the spindle rotation started, and a thickening was scored in accordance with the following criteria.

A: >7 Pas, Stable thickened composition
B: 3 to 7 Pas, Relatively stable thickened composition and no practical problem
C: <3 Pas, Not stable thickened composition The results of the evaluations are shown in Table 11.

TABLE 11

| | | Manufacturing Example | |
| --- | --- | --- | --- |
| | | 1 | 2 |
| Emulsion (step (ii)) | pH | 6.8 | 9.7 |
| | Viscosity | B | B |
| Composition (Step (iii)) | pH | 10.5 | 10.5 |
| | Viscosity | A | B |
| | Sniff Test | 1 | 3 |

As shown in Table 11, the composition prepared according to Preparation Protocol (i) comprising adding. (d) alkaline agents to the emulsion obtained in step (ii) shows substantially reduced ammonia odor and improved stability with its increased viscosity. In contrast, the composition prepared according to Preparation Protocol (ii) comprising adding alkaline agent (d1) (ethanol amine) with water to the oil phase in step (ii), i.e. changing the pH value of the mixture to alkaline$_T$H before the emulsion is formed, has relatively more ammonia odor and lower stability compared to that of Preparation Protocol (i). However, the composition prepared according to Preparation Protocol (ii) can also suppress the ammonia odor and keeps good stability relatively compared to the conventional compositions for the keratin fibers.

FIG. 1 shows a microscopic photography of the mixture of the composition prepared according to Manufacturing Protocol (i). FIG. 1(a) shows the emulsion before the alkaline agents were added. FIG. 1(b) shows the composition after the alkaline agents were added and mixed. Scale bar is 50 μm. According to these pictures, it can be observed that before adding the alkaline agents, there were many bulky and liquid regions in the continuous phase 1, and after adding the alkaline agents, the continuous phase 2 was structured.

The invention claimed is:

1. A hair treatment composition comprising:
    (a) at least one non-neutralized anionic surfactant chosen from fatty carboxylic acids, fatty ether carboxylic acids, N-acylamino acids, or mixtures thereof, wherein the fatty carboxylic acids are represented by formula (I):

in which R is a linear and saturated hydrocarbon radical containing from 6 to 40 carbon atoms;
    (b) at least one non-ionic surfactant chosen from monooxyalkylenated, polyoxyalkylenated, monoglycerolated, polyglycerolated nonionic surfactants, or mixtures thereof, wherein the at least one non-ionic surfactant comprises at least one non-ionic surfactant comprising 10 to 100 oxyalkylene units;
    (c) at least one fatty alcohol corresponding to structure R—OH, wherein R is chosen from saturated and unsaturated, linear and branched radicals containing from 8 to 40 carbon atoms;
    (d) an alkaline-component comprising ammonia and/or a salt thereof, and optionally at least one additional alkaline agent, and
    (e) at least one hair dyeing agent or hair permanent waving agent,
    wherein the hair treatment composition comprises less than about 2% by weight of a phosphoric surfactant, relative to the total weight of the hair treatment composition, and
    wherein the hair treatment composition is formed from (i) a first composition in the form of an emulsion comprising water and oil phases, further comprising (a) at least one non-neutralized anionic surfactant, (b) at least one non-ionic surfactant and (c) at least one fatty alcohol, (ii) a second composition comprising (d) an alkaline component comprising ammonia and/or a salt thereof, and optionally (iii) at least one additional composition,
    wherein the first composition has a pH below a pKa of at least one non-neutralized anionic surfactant and does not comprise a neutralizing agent in an amount sufficient to neutralize the anionic surfactant(s),
    wherein one or more of the first, second, or optional additional compositions comprise (e) at least one hair dyeing agent or hair permanent waving agent,
    wherein the first composition is free of ammonia and is free of salts of ammonia, and
    wherein the hair treatment composition comprises a total amount of ammonia and/or salts thereof ranging from 0.1% to 20% by weight, relative to the total weight of the hair treatment.

2. The hair treatment composition according to claim 1 wherein the at least one non-neutralized anionic surfactant is present in an amount ranging from about 0.01% to about 20% by weight, relative to the total weight of the hair treatment composition.

3. The hair treatment composition according to claim 1 wherein the at least one non-ionic surfactant is present in an amount ranging from about 0.1% to about 20% by weight, relative to the total weight of the hair treatment composition.

4. The hair treatment composition according to claim 1 wherein the at least one fatty alcohol is chosen from lauryl alcohol, cetyl alcohol, stearyl alcohol, oleyl alcohol, behenyl alcohol, linoleyl alcohol, undecylenyl alcohol, palmitoleyl alcohol, arachidonyl alcohol, erucyl alcohol, cetearyl alcohol, or mixtures thereof.

5. The hair treatment composition according to claim 1 wherein the at least one fatty alcohol is present in an amount ranging from about 0.1% to about 40% by weight, relative to the total weight of the hair treatment composition.

6. The hair treatment composition according to claim 1, wherein the total amount of the alkaline component ranges from about 0.1% to about 20% by weight, relative to the total weight of the hair treatment composition.

7. The composition according to claim 1 wherein the viscosity of the hair treatment composition is at least 3 Pa·s at 25° C.

8. The hair treatment composition according to claim 1 wherein the at least one hair dyeing agent or hair permanent waving agent is chosen from oxidation dyes, direct dyes, or reducing agents.

9. A method for treating hair, comprising applying to the hair a hair treatment composition comprising:
(a) at least one non-neutralized anionic surfactant chosen from fatty carboxylic acids, fatty ether carboxylic acids, N-acylamino acids, or mixtures thereof, wherein the fatty carboxylic acids are represented by formula (I):

RCOOH    (I), in which R is a linear and saturated hydrocarbon radical containing from 6 to 40 carbon atoms;
(b) at least one non-ionic surfactant chosen from monooxyalkylenated, polyoxyalkylenated, monoglycerolated, polyglycerolated nonionic surfactants, or mixtures thereof, wherein the at least one non-ionic surfactant comprises at least one non-ionic surfactant comprising 10 to 100 oxyalkylene units;
(c) at least one fatty alcohol corresponding to structure R—OH, wherein R is chosen from saturated and unsaturated, linear and branched radicals containing from 8 to 40 carbon atoms;
(d) an alkaline component comprising ammonia and/or a salt thereof, and optionally at least one additional alkaline agent; and
(e) at least one hair dyeing agent or hair permanent waving agent,
wherein the hair treatment composition comprises less than about 2% by weight of a phosphoric surfactant, relative to the total weight of the hair treatment composition, and
wherein the hair treatment composition is formed from (i) a first composition in the form of an emulsion comprising water and oil phases, further comprising (a) at least one non-neutralized anionic surfactant, (b) at least one non-ionic surfactant and (c) at least one fatty alcohol, (ii) a second composition comprising (d) an alkaline component comprising ammonia and/or a salt thereof, and optionally (iii) at least one additional composition,
wherein the first composition has a pH below a pKa of at least one non-neutralized anionic surfactant and does not comprise a neutralizing agent in an amount sufficient to neutralize the anionic surfactant(s),
wherein one or more of the first, second, or optional additional compositions comprise (e) at least one hair dyeing agent or hair permanent waving agent,
wherein the first composition is free of ammonia and is free of salts of ammonia, and
wherein the hair treatment composition comprises a total amount of ammonia and/or salts thereof ranging from 0.1% to 20% by weight, relative to the total weight of the hair treatment composition.

10. The method according to claim 9, furthering comprising applying a mechanical tension to the hair before applying the composition.

11. The hair treatment composition according to claim 1, wherein the pH of the hair treatment composition ranges from 9 to 12.

12. The hair treatment composition according to claim 1, wherein the first composition further comprises at least one non-ionic surfactant.

13. The hair treatment composition according to claim 1, wherein the first composition comprises at least one non-neutralized anionic surfactant chosen from fatty carboxylic acids of formula (I).

14. The hair treatment composition according to claim 1, wherein the first composition comprises at least one non-neutralized anionic surfactant chosen from capric acid, caprylic acid, lauric acid, oleic acid, isostearic acid, stearic acid, oleth-10 carboxylic acid, laureth-5 carboxylic acid, laureth-11 carboxylic acid, cocoyl glutamic acid, cocoyl sarcosine, lauroyl methyl-β-alanine, myristoyl methyl-β-alanine, or mixtures thereof.

15. The hair treatment composition according to claim 1, further comprising at least one non-silicone fatty substance.

16. The hair treatment composition according to claim 15, wherein the at least one non-silicone fatty substance is chosen from alkanes, fatty acid esters, fatty alcohol esters, liquid paraffin, mineral oils, plant oils, animal oils, synthetic oils, non-silicone waxes, or mixtures thereof.

17. The hair treatment composition according to claim 15, wherein the at least one non-silicone fatty substance is present in the hair treatment composition in an amount ranging from 0.1% to 30% by weight, relative to the total weight of the hair treatment composition.

* * * * *